US011338039B2

(12) United States Patent
Boschetti et al.

(10) Patent No.: US 11,338,039 B2
(45) Date of Patent: May 24, 2022

(54) ABUSE-PROOF SOLID PHARMACEUTICAL COMPOSITION

(71) Applicant: E-Pharma Trento S.p.A., Frazione Ravina (IT)

(72) Inventors: Silvia Boschetti, Aldeno (IT); Massimiliano Rossi, Trento (IT); Diego Benfenati, Caldonazzo (IT); Alessandro Pojer, Altavalle (IT)

(73) Assignee: E-Pharma Trento S.p.A., Frazione Ravina (IT)

(*) Notice: Subject to any disclaimer, the term of this patent is extended or adjusted under 35 U.S.C. 154(b) by 136 days.

(21) Appl. No.: 15/828,684

(22) Filed: Dec. 1, 2017

(65) Prior Publication Data

US 2018/0154002 A1    Jun. 7, 2018

(30) Foreign Application Priority Data

Dec. 2, 2016  (IT) .................. 102016000122469

(51) Int. Cl.
| A61K 47/36 | (2006.01) |
| A61K 47/02 | (2006.01) |
| A61K 31/485 | (2006.01) |
| A61K 9/00 | (2006.01) |
| A61K 31/192 | (2006.01) |
| A61K 45/06 | (2006.01) |
| A61K 9/16 | (2006.01) |
| A61K 9/20 | (2006.01) |

(52) U.S. Cl.
CPC ............ *A61K 47/36* (2013.01); *A61K 9/0095* (2013.01); *A61K 9/1623* (2013.01); *A61K 9/205* (2013.01); *A61K 9/2009* (2013.01); *A61K 9/2018* (2013.01); *A61K 31/192* (2013.01); *A61K 31/485* (2013.01); *A61K 45/06* (2013.01); *A61K 47/02* (2013.01); *A61K 2300/00* (2013.01)

(58) Field of Classification Search
CPC ...................................................... A61K 47/36
See application file for complete search history.

(56) References Cited

U.S. PATENT DOCUMENTS

| 2008/0203199 A1* | 8/2008 | Serafin ............... C08B 37/0096 241/5 |
| 2010/0015219 A1 | 1/2010 | Berleur et al. |
| 2012/0148672 A1 | 1/2012 | Mehta et al. |
| 2015/0320690 A1* | 11/2015 | Friedrich ............... A61K 9/485 424/452 |

FOREIGN PATENT DOCUMENTS

| WO | WO-03039561 A1 * | 5/2003 | ......... A61K 31/485 |
| WO | 2008/150526 | 12/2008 | |

OTHER PUBLICATIONS

Takeiti et al., Morphological and Physicochemical Characterization of Commercial Maltodextrins with Different Degrees of Dextrose-Equivalent, 2010, International Journal of Food Properties, 13, pp. 411-425 (Year: 2010).*
Alzqhari et al. Cureus, 2017, 9(9): e1679.*
Search Report in Application No. IT201600122469 dated Dec. 2, 2016.
Allen, Loyd, "Oxycodone Hydrochloride 1 mg/mL Oral Liquid", (Oct. 19, 2011), pp. 1-3, XP55396223.

* cited by examiner

*Primary Examiner* — Rei Tsang Shiao
(74) *Attorney, Agent, or Firm* — Oblon, McClelland, Maier & Neustadt, L.L.P.

(57) ABSTRACT

The present invention relates to an abuse-proof solid pharmaceutical composition comprising an active ingredient with potential for abuse, silica in an amount of from 10 mg to 1000 mg, guar flour in an amount of from 100 mg to 300 mg, and a water soluble diluent in an amount of from 500 mg to 5000 mg.

18 Claims, No Drawings

ABUSE-PROOF SOLID PHARMACEUTICAL COMPOSITION

FIELD OF THE INVENTION

The present invention relates to an abuse-proof solid pharmaceutical composition, in particular a solid pharmaceutical composition, such as, for example a granulate or a tablet, capable of solubilizing in a glass of water (about 100 ml), but of forming a not injectable gel and/or viscous solution if added to the amount of water contained in a hypodermic syringe (about 10 ml).

PRIOR ART

Many active pharmaceutical ingredients, besides having an excellent therapeutic activity in their suitable therapeutic prescription, also have a potential for abuse, i.e. can be used inappropriately by a user to achieve different effects from those expected. Opiates, for example, which are highly active in the treatment of severe or very severe pain, are often used by drug addicts to induce a state of narcosis or euphoria, in jargon called "buzz".

Pharmaceutical compositions containing active ingredients with potential for abuse, even if taken orally in large quantities, usually do not give rise to buzz, because blood levels of active ingredients increase slowly.

However, to get the buzz, the user pulverizes the corresponding pharmaceutical compositions, such as through grinding, and extracts the active ingredient from the powder thus obtained with the aid of a liquid, usually water, preferably in the minimum amount required to use in a hypodermic syringe. The resulting solution, possibly after filtration through cellulose wadding or cotton, is administered parenterally, particularly intravenously.

The parenteral administration of minimal amounts of aqueous solution causes a rapid increase in blood levels of the active ingredient, providing the user with the quick narcotic effect desired.

The practice of using drugs containing opiates such as oxycodone or oxymorphone to produce injectable aqueous solutions is very prevalent among drug addicts. Other substances able to provide an effect similar to buzz are contained in different stimulant drugs, such as for example amphetamines, or tranquilizers, such as for example benzodiazepines and barbiturates.

To prevent abuse of drugs containing substances with potential for abuse, the FDA (Food and Drug Administration), the U.S. federal body for the registration and regulation of drugs, issued new directives with the aim of assisting companies in developing medicines that—in addition to providing the necessary guarantees of efficacy and safety when used according to the prescriptions of the physician— have features that exert a deterrent action such as to discourage abuse and misuse.

The techniques known in the art to discourage the abuse can be grouped into five categories depending on the approach used. A first approach is to add a gelling or thickening agent to the pharmaceutical composition, making it impossible to attempt to abuse the formulation by solubilisation in water. Alternately, a material with high mechanical strength is used that makes it impossible to attempt to abuse the formulation by grinding and inhaling. A third way is to introduce an agent able to antagonize and void the effect of the active ingredient comprised in the formulation if administered in different ways than expected. In addition, a sort of physical protection of the active ingredient is also made through a coating layer of hydrophobic substances which makes impossible the solubilisation. One last technique involves the addition of pollutants, for example irritants, which make taking the formulation by inhalation and/or injection unpleasant.

A number of patents and patent applications describe abuse-proof solid formulations including gelling or thickening agents.

WO2014/140231 relates to a liquid formulation comprising an active ingredient, a thickening agent and a surfactant, which when mixed with water and heated, forms a viscous mixture not injectable. Thickening agents included acacia gum, pectin, agar, tragacanth, xanthan gum, guar gum, carob flour, tara gum, karaya gum, gellan gum.

WO2013/030177 relates to an abuse-proof tablet including an active layer comprising oxycodone and acetaminophen and a gelling layer comprising hydroxypropyl methylcellulose.

WO95/20947 relates to an abuse-proof tablet comprising two or more layers, where one or more substances with potential for abuse and one or more gelling substances are contained in separate layers. The gelling substances included modified cellulose, sodium alginate, alginic acid, polyacrylic acid, tragacanth, xanthan gum, guar gum, and carob flour.

WO2008/150526 relates to a delivery system consisting of a lipid solid suspension comprising, in addition to an active substance, at least one gelling agent and a lipid in a weight ratio of less than 1:1.4.

WO2014/123899 describes a solid dosage form, in particular a tablet, containing a heat-labile gelling agent, in particular xanthan gum, a heat stabilizer, in particular carbomer (crosslinked homopolymers of acrylic acid) and a substance with potential for abuse.

SUMMARY OF THE INVENTION

The Applicant has noted that abuse-proof pharmaceutical forms known in the art are represented by tablets, capsules or other solid forms to be swallowed as such.

The pharmaceutical forms of this type can cause problems in people with swallowing difficulties, especially in older people, who are also the people most concerned in the taking of analgesic drugs containing opiates for the treatment of severe and/or very severe pain.

The Applicant then faced the problem of creating an abuse-proof pharmaceutical composition to be administered orally after dissolving in water, but which at the same time does not allow parenteral administration.

The Applicant has found that guar flour and other known gelling substances used alone were not able to solve the problem addressed.

In particular, for example, the guar flour at the doses required for obtaining a solution free of agglomerates and visually acceptable for use in a volume of 100 ml of water, typically less than 200 mg, does not guarantee non-injectability if dispersed in 10 ml, while at a quantity equal to or greater than 200 mg, able to guarantee the non-injectability, it forms clearly visible and not aesthetically acceptable agglomerates for administration in a volume of 100 ml of water.

In an attempt to solve the faced problem, the Applicant surprisingly found that a mixture of silica and guar flour suitably dosed and mixed was capable of solubilizing in a glass of water (about 100 ml), but of forming a gel and/or a viscous solution not injectable if added to the amount of water contained in a hypodermic syringe (about 10 ml).

Continuing the experimentation, the Applicant also surprisingly found that by using the above mixture of silica and guar flour with an active ingredient with potential for abuse, such as an opiate like oxycodone, and at least one water-soluble diluent it was possible to make an abuse-proof solid pharmaceutical composition soluble in the amount of water commonly contained in a glass (about 100 ml), thus allowing the oral administration after dissolving in water.

At the same time, the Applicant has surprisingly found that the abuse-proof solid pharmaceutical composition thus made formed a not injectable gel and/or viscous solution if added to the amount of water contained in a hypodermic syringe (about 10 ml), thus preventing the parenteral administration and preventing abuse.

In addition, the Applicant has noted that the above viscous solution showed an extremely high osmolarity, well above the normal serum osmolarity of about 300 mOsM, this constituting an additional obstacle to parenteral administration.

At the end of experimentation, the Applicant surprisingly found that although a solution of silica in 10 ml maintains the injectability also for an amount of silica that equals one gram, the mixture of 200 mg guar flour with just 50 mg anhydrous silica or 100 mg hydrated silica dispersed in 10 ml led to the formation of a non-injectable gel.

Even more surprisingly, the Applicant found that the addition of a water-soluble diluent, such as maltodextrin, in order to achieve a water-soluble granulate and/or tablet, did not significantly alter the result obtained with the combination of only silica and guar flour, which was maintained by increasing to 100 mg the amount of anhydrous silica and to 150 or 200 mg the amount of guar flour.

The present invention therefore relates to an abuse-proof solid pharmaceutical composition comprising an active ingredient with potential for abuse, silica in an amount of from 10 mg to 1000 mg, guar flour in an amount of from 100 mg to 300 mg, and a water soluble diluent in an amount of from 500 mg to 5000 mg.

DETAILED DESCRIPTION OF THE INVENTION

The abuse-proof solid pharmaceutical composition of the present invention comprises at least one active ingredient with potential for abuse.

The active ingredient with potential for abuse used in the present invention may be any active ingredient with potential for abuse, preferably selected from opioids, tranquillisers (anti-anxiety and anti-psychotics), stimulants and narcotics.

The opioids usable in present invention are preferably selected from alfentanil, allilprodine, alphaprodine, anileridine, benzylmorphine, bezitramide, buprenorphine, butorphanol, clonitazene, codeine, cyclazocine, desomorphine, dextromoramide, dextropropoxyphene, dezocine, diamorphone, diampromide, dihydrocodeine, dihydromorphine, dimenoxadolo, dimepheptanol, dimethylthiambutene, dipipanone, eptazocine, etorphine, dihydroetorphine, ethylmethyltiambutene, ethylmorphine, heroin, fentanyl, hydrocodone, hydromorphone, isomethadone, ketobemidone, levorphanol, lofentanil, meperidine (pethidine), meptazinol, metazocine, methadone, metopon, morphine, nalbuphine, narceine, nicomorphine, norlevorphanol, normethadone, nalorphine, normorphine, norpipanone, oxycodone, oxymorphone, pentazocine, phenadoxone, phenomorphan, phenazocine, phenoperidine, piminodine, piritramide, propheptazine, promedol, properidine, propiram, propoxyphene, sufentanil, tramadol, tilidine and mixtures thereof.

Preferably, the opioids useful in present invention are oxycodone, oxymorphone, and mixtures thereof.

Active ingredients with potential for abuse include amphetamines, such as for example amphetamine, amphepramone, bupropion, cathine, cathinone, clobenzorex, ephedrine, phenylethylamine, phentermine, foledrine, methamphetamine, methylenedioxymethamphetamine (MDMA), norfenfluramine, norpholedrine, ortetamine, pirovalerone, and pseudoephedrine, and barbiturates, such as for example allobarbital, amobarbital, aprobarbital, alfenal, barbital, brallobarbital, butobarbital, hexobarbital pentobarbital, phenobarbital, secobarbital, thiopental, and talbutal.

Other active principles with potential for abuse are benzodiazepines, such as alprazolam, bromazepam, clonazepam, clorazepate, diazepam, estazolam, flurazepam, flunitrazepam, lorazepam, nitrazepam, oxazepam, temazepam and triazolam.

Further active principles with potential for abuse are mebicar, fabomotizole, selank, bromantane, emoxypine, azapiron (buspirone), hydroxyzine, pregabalin, and propofol.

The abuse-proof solid pharmaceutical composition of the present invention may also contain a secondary active ingredient, without potential for abuse, such as for example an analgesic.

Examples of analgesics usable in the present invention are, for example, paracetamol, non-steroidal anti-inflammatory drugs (NSAIDs) and cyclo-oxygenase-2 (COX-2) inhibitors.

Suitable NSAIDs usable in present invention are, for example, aspirin, benzydamine, ibuprofen, diclofenac, naproxen, flurbiprofen, fenoprofen, ketoprofen, ketorolac, indoprofen, piroprofen, carprofen, oxaprozin, pramoprofen, muroprofen, suprofen, aminoprofen, tiaprofenic acid, fluprofen, indomethacin, benzadac, sulindac, ibufenac, tolmetin, zomepirac, tiopinac, zidomethacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, and isoxicam.

Suitable COX-2 inhibitors usable in the present invention are, for example, celecoxib, parecoxib, etoricoxib, firocoxib, flosulide, meloxicam, nabumetone, and nimesulide.

Preferably, the secondary active ingredient in the composition of the present invention is selected from the group consisting of aspirin, acetaminophen, ibuprofen, or ketoprofen.

The active ingredients contained in the pharmaceutical composition of the present invention, both those with potential for abuse and the secondary ones, may be present in their free form or as a salt with a pharmaceutically acceptable acid or base.

The active ingredients including an acid function can be transformed in their salt with a pharmaceutically acceptable organic or inorganic base, such as methylamine, dimethylamine, trimethylamine, ethylamine, diethylamine, triethylamine, propylamine, dipropylamine, tripropylamine, ethylenediamine, monoethanolamine, diethanolamine, triethanolamine, guanidine, morpholine, piperidine, pyrrolidine, piperazine, 1-butylpiperidine, 1-ethyl-2-methylpiperidine, N-methylpiperazine, 1,4-dimethylpiperazine, N-benzylphenethylamine, N-methylglucosamine, tris (hydroxymethyl) aminomethane, ammonia, sodium hydroxide, calcium hydroxide, potassium hydroxide, aluminium hydroxide, iron hydroxide, magnesium hydroxide, zinc hydroxide, arginine and lysine.

The active ingredients including a basic function can be transformed in their salt with a pharmaceutically acceptable organic or inorganic acid such as acetic acid, ascorbic acid, oxalic acid, succinic acid, maleic acid, fumaric acid, tartaric acid, methanesulfonic acid, paratoluenesulfonic acid, citric acid, lactic acid, tannic acid, benzoic acid, aspartic acid, glutamic acid, hydrochloric acid, hydrobromic acid, phosphoric acid, sulfuric acid and nitric acid.

The abuse-proof solid pharmaceutical composition of the present invention comprises silica in an amount of from 10 mg to 1000 mg, guar flour in an amount of from 100 mg to 300 mg, and a water soluble diluent in an amount of from 500 mg to 5000 mg.

Preferably, the abuse-proof solid pharmaceutical composition of the present invention comprises silica in an amount of from 50 mg to 500 mg, more preferably from 100 mg to 300 mg.

Preferably, the silica used in the composition of the present invention is anhydrous silica or hydrated silica.

Advantageously, the abuse-proof solid pharmaceutical composition of the present invention comprises anhydrous silica in an amount of from 50 mg to 100 mg, or hydrated silica in an amount of from 100 mg to 200 mg.

The guar flour or gum is the product of grinding the endosperm of guar seeds *Cyamopsis tetragonoloba*, an herbaceous plant of legume crops typical of the region of India and Pakistan. The main component is a galactomannan, a trisaccharide composed of galactose and mannose units, polymerized to form α-D-mannopyranosil chains bound with a glycosidic bond β-D-(1-4) and having molecular weight of between 200,000 and 300,000 Dalton, to form a linear chain 1-4 with short lateral branches 1-6 of galactose, with a galactose/mannose ratio of about 2:1. Guar gum is also called guaran or often abbreviated as GG.

Preferably, the abuse-proof solid pharmaceutical composition of the present invention comprises guar flour in an amount of from 150 mg to 250 mg, advantageously in an amount of about 200 mg.

Preferably, the guar flour useful in present invention has a fine granulometry, with an average diameter of less than 100 µm, preferably less than 80 µm. On the basis of experience gained from the present invention, the Applicant in fact believes that a guar flour with granulometry greater than 100 µm is not suitable for the purposes of the present invention.

Advantageously, the guar flour useful in the present invention has an average diameter of from 10 µm to 80 µm, and particularly from 30 µm to 80 µm.

Preferably, the abuse-proof solid pharmaceutical composition of the present invention comprises a water-soluble diluent in an amount of from 1000 mg to 4000 mg, more preferably from 1500 mg to 3500 mg.

Advantageously, the abuse-proof solid pharmaceutical composition of the present invention comprises a water-soluble diluent in an amount of from 2000 mg to 3000 mg.

Water-soluble diluents preferably used in the pharmaceutical composition of the present invention are, for example, maltodextrins, sucrose powder, crystalline sucrose, lactose, dextrose, mannitol, sorbitol, xylitol, etc.

Advantageously, the preferred water-soluble diluent is selected from the group consisting of maltodextrin with DE of between 10 and 20, preferably between 15 and 20, sucrose powder, and crystalline sucrose.

Preferably, the water-soluble diluent useful in present invention has a fine granulometry, with an average diameter of less than 500 µm, preferably less than 400 µm. On the basis of experience gained from the present invention, the Applicant in fact believes that a water-soluble diluent with granulometry greater than 500 µm is not suitable for the purposes of the present invention.

Advantageously, the water-soluble diluent useful in the present invention has an average diameter of from 20 µm to 350 µm, and particularly from 40 µm to 300 µm.

The pharmaceutical composition of the present invention may include other ingredients typically used in the preparation of formulations to be taken orally such as, for example, pH regulators, buffering agents, sweeteners, flavourings, and the like.

Examples of suitable pH regulators are for example sodium bicarbonate, calcium carbonate, magnesium carbonate, sodium phosphate, sodium citrate, and the like.

Useful examples of buffering agents are represented by basic sodium phosphate, dibasic sodium phosphate, citrate buffer (sodium citrate/citric acid), and the like.

Examples of suitable sweetening agents include aspartame, saccharin, acesulfame, and so on.

Examples of suitable flavoring agents include grapefruit flavor, raspberry flavor, lemon flavor, orange flavor, caramel flavor, vanilla flavor, cream flavor, and the like.

The pharmaceutical composition of the present invention may be formulated as a tablet, granulate, or water-soluble powder to be taken orally after dissolution in the appropriate volume of water, preferably about 100 ml, namely the volume contained in a standard glass.

The pharmaceutical composition of the present invention may also be formulated in effervescent compositions. In this case, effervescent agents are added to the composition. Effervescent agents typically comprise an acid-base pair able to develop a gas when dissolved in water. Useful examples of effervescent agents are represented by acid-base pairs comprising an organic acid such as, for example, citric acid, tartaric acid, malic acid, fumaric acid, adipic acid, succinic acid, and mixtures thereof, and a carbonate or bicarbonate of alkali or alkaline earth metal such as, for example, calcium carbonate, sodium bicarbonate, sodium sesquicarbonate, and mixtures thereof.

The pharmaceutical composition of the present invention, when dissolved in about 10 mL of water shows osmolarity equal to or greater than 600 mOsm, preferably equal to or greater than 800 mOsm, and more preferably ranging from 800 to 1,500 mOsm.

The following examples are intended to further illustrate the present invention without limiting it in any way.

EXAMPLES

In the following examples, injectability tests and solubility tests were conducted.

Injectability tests were conducted using a 10 ml syringe with G21 needle (green) with nominal outside diameter of 0.8 mm or G18 needle (pink) with nominal outside diameter of 1.2 mm. The tests were always conducted at 22° C. filling the syringe with 10 ml of the solution under examination and placing the syringe vertically on a dedicated holder. The test is conducted by measuring the time taken to complete the spill of 10 ml of solution from the time a 1 kg weight is placed on the plunger, or noting the failure to pass.

Solubility tests were conducted by dissolving or trying to dissolve increasing amounts of the composition in 100 ml of deionized water at 22° C. The resulting solution or dispersion was observed visually and photographed under a digital microscope (27×). The visual inspection of the appearance of the resulting dispersion or solution was scored from 1 to 4, respectively good, sufficient, insufficient, bad. The digital microscopic examination examined whether agglomerations were present or not.

Example 1

Guar Flour

Increasing amounts of guar flour were used to test solubility and injectability.

The amounts of guar flour employed to carry out the solubility test are shown in the following Table 1 together with the obtained results.

TABLE 1

| Quantity (mg) | Visual evaluation | Digital microscopy evaluation-Agglomerates |
|---|---|---|
| 50 | 1 | No |
| 200 | 2 | No |
| 250 | 2 | Yes |
| 300 | 4 | Yes |

The solubility test therefore indicated a maximum amount of 200 mg of guar flour in order to obtain an acceptable solution in 100 ml.

To carry out the injectability test, four different batches of guar flour were used from different suppliers with different granulometry, as shown in the following Table 2. The previous solubility test had been performed with batch 1.

TABLE 2

| Batch | Average granulometry (μm) | Fraction < 75 μm (%) | Fraction > 500 μm (%) |
|---|---|---|---|
| 1 | 68.09 | 53.91 | 0.00 |
| 2 | 54.78 | 63.72 | 0.00 |
| 3 | 116.3 | 16.10 | 0.00 |
| 4 | 53.5 | 65.75 | 0.00 |

The amounts of guar flour used for each batch are shown in the following Table 3 together with the obtained results. A first test conducted with water alone was conducted as a reference (R).

TABLE 3

| | | G21 needle | | G18 needle |
|---|---|---|---|---|
| Batch | Quantity(mg) | Passage | Time | Passage |
| R | 0 | Yes | 14 | Yes |
| 1 | 50 | Yes | 18 | Yes |
| | 75 | Yes | 20 | Yes |
| | 100 | Yes | 25 | Yes |
| | 125 | Yes | 41 | Yes |
| | 150 | Yes | 60 | Yes |
| | 175 | Yes | 107 | Yes |
| | 200 | No | — | Yes |
| 2 | 50 | Yes | 17 | Yes |
| | 100 | Yes | 25 | Yes |
| | 150 | Yes | 63 | Yes |
| 3 | 50 | Yes | 13 | Yes |
| | 100 | Yes | 23 | Yes |
| | 150 | Yes | 27 | Yes |
| 4 | 50 | Yes | 17 | Yes |
| | 100 | Yes | 22 | Yes |
| | 150 | Yes | 65 | Yes |

The injectability test conducted up to 200 mg showed that with guar flour alone it was not possible to make a composition that was soluble in 100 ml water and at the same time not injectable if dissolved in 10 ml of water.

The obtained results suggested that the granulometry affects the thickening capability. Batch 3 showing the highest average granulometry was the batch with lower thickening capability.

Example 2

Anhydrous Silica

Increasing amounts of anhydrous silica were used to test solubility and injectability.

To carry out the solubility test, the amounts of anhydrous silica shown in the following Table 4 together with the obtained results were used.

TABLE 4

| Quantity (mg) | Visual evaluation | Agglomerates |
|---|---|---|
| 1000 | 1 | No |
| 2000 | 2 | No |
| 4000 | 3 | Yes |
| 6000 | 4 | Yes |

The solubility test therefore indicated a maximum amount of 2000 mg of anhydrous silica in order to obtain an acceptable solution in 100 ml. These amounts showed the good solubility of anhydrous silica in water, and a poor thickening effect was predicted for amounts of less than 1000 mg.

The amounts of anhydrous silica employed to carry out the injectability test are shown in the following Table 5 together with the obtained results.

TABLE 5

| Quantity | G21 needle | | G18 needle |
|---|---|---|---|
| (mg) | Passage | Time | Passage |
| 100 | Yes | 14 | Yes |
| 200 | Yes | 17 | Yes |
| 300 | Yes | 45 | Yes |
| 500 | Yes | 48 | Yes |
| 600 | Yes | 60 | Yes |
| 750 | Yes | 300 | Yes |

The results of the injectability test confirmed the unsuitability of anhydrous silica for the intended objects. The amounts of anhydrous silica necessary to obtain a non-injectable solution would have created a solution, although visually acceptable, with poor palatability.

Example 3

Hydrated Silica

Injectability and solubility tests performed with hydrated silica did not produce significantly different and better results than those obtained with anhydrous silica. In contrast, hydrated silica proved even more soluble with a lower thickening effect also with quantities up to 1000 mg that showed the passage to the injectability test with G21 needle within 64 seconds.

Example 4

Xanthan Gum

Solubility tests performed with xanthan gum produced, already with low quantities, visually insufficient dispersions with the presence of several agglomerates. This product was therefore discarded without further testing.

Example 5

Binary Combinations

The injectability test was repeated using 200 mg of guar flour mixed with the amounts of hydrated silica or anhydrous silica given in following tables 6a and 6b together with the obtained results. The guar flour used corresponded to batch 1 of example 1.

TABLE 6A

| Anhydrous silica | G21 needle | | G18 needle | |
|---|---|---|---|---|
| (mg) | Passage | Time | Passage | Time |
| 25 | No | — | Yes | 13 |
| 50 | No | — | No | — |
| 75 | No | — | No | — |
| 100 | No | — | No | — |

TABLE 6b

| Hydrated silica | G21 needle | | G18 needle | |
|---|---|---|---|---|
| (mg) | Passage | Time | Passage | Time |
| 50 | No | — | Yes | 12 |
| 75 | No | — | Yes | 35 |
| 100 | No | — | No | — |

The obtained results surprisingly showed that relatively small amounts of silica, well below those required if used alone, have a synergistic and disruptive effect in combination with guar flour.

The Applicant has in fact surprisingly noted that with a G18 needle using anhydrous silica in an amount of 25 mg there was a passage in a short time, while increasing the amount to 50 mg, instead of observing, as one would have expected, a moderate increase in the time of passage, a sharp increase in the viscosity of the solution was observed which resulted in no passage.

Similarly, the Applicant surprisingly observed that the same sharp increase in the viscosity of the solution also occurred with hydrated silica passing from the amount of 75 mg to the amount of 100 mg.

The solubility test conducted with the mixture of 200 mg guar flour and 100 mg anhydrous or hydrated silica produced optimal results in both cases, with a visual assessment of 1 (good) and the total absence of agglomerates visible at the digital microscope (27×).

Example 6

Water-Soluble Diluent

In order to make a pharmaceutical composition, several water-soluble diluents were tested in combination with 100 mg of anhydrous silica and 200 mg of guar flour. The type and amount of water-soluble diluent is shown in the following Table 7 together with the results obtained in the solubility and injectability tests.

TABLE 7

| Diluent | Quantity (mg) | Injectability with G18 needle | Solution appearance |
|---|---|---|---|
| Sorbitol | 3000 | No | 1 |
| Sucrose | 3000 | No | 1 |
| Lactose | 3000 | No | 1 |
| Maltodextrin | 3000 | No | 1 |

The data summarized in table 7 showed that commonly used diluents did not affect the appearance of the solution in the solubility test and retained the non-injectability also with G18 needle.

Example 7

Pharmaceutical Composition

On the basis of the obtained results, a formulation of a water-soluble granulate containing ibuprofen and oxycodone was prepared. The qualitative and quantitative composition of the formulation is shown in the following Table 8.

TABLE 8

| Components | Quantity (mg) |
|---|---|
| Sodium ibuprofen | 512 |
| Oxycodone | 20 |
| Sodium bicarbonate powder | 50 |
| Natural lemon flavoring | 70 |
| Anhydrous silica | 100 |
| Acesulfame K | 70 |
| Maltodextrin | 2988 |
| Guar flour | 200 |
| Granulate | 2100 |
| Total | 6110 |

The granulate used in the preparation of the formulation was previously prepared by wet granulation of 100 mg of ascorbic acid, 1,000 mg of powdered sucrose and 1,000 mg of crystalline sucrose.

The formulation of Table 8 was subjected to the same injectability and solubility tests described above. The results are summarized in the following Table 9.

TABLE 9

| Injectability with G21 needle | Injectability with G18 needle | Solution appearance |
|---|---|---|
| No | No | 1 |

The osmolarity of the solution obtained by dissolving the formulation of Table 8 in 10 ml of deionized water, measured with Gonotec Osmomat 030 osmometers, was equal to about 855 mOsm.

The invention claimed is:
1. An abuse-proof solid pharmaceutical composition comprising an active ingredient with potential for abuse, silica in an amount of from 100 mg to 300 mg, guar flour in an amount of from 100 mg to 300 mg, and a water soluble diluent in an amount of from 1000 mg to 4000 mg;

wherein the active ingredient with potential for abuse is an opioid;

wherein said silica and said guar flour are present in relative amounts such that the solid pharmaceutical composition is soluble in 100 ml of water, but the solid pharmaceutical composition forms a non-injectable gel or non-injectable viscous solution if placed in 10 ml of water, and wherein said opioid is at least one member selected from the group consisting of alfentanil, allilprodine, alphaprodine, benzylmorphine, butorphanol, clonitazene, codeine, cyclazocine, desomorphine, dextromoramide, dextropropoxyphene, dezocine, diamorphine, diampromide, dihydrocodeine, dihydromorphine, dimenoxadolo, dimepheptanol, dimethylthiambutene, dipipanone, eptazocine, etorphine, dihydroetorphine, ethylmethyltiambutene, ethylmorphine, heroin, fentanyl, hydrocodone, hydromorphone, isomethadone ketobemidone, levorphanol, lofentanil, meperidine (pethidine), meptazinol, metazocine, methadone, metopon, morphine, nalbuphine, narceine, nicomorphine, norlevorphanol, normethadone, nalorphine, normorphine, norpipanone, oxycodone, oxymorphone, pentazocine, phenadoxone, phenomorphan, phenazocine, phenoperidine, piminodine, piritramide, propheptazine, promedol, properidine, propiram, propoxyphene, sufentanil, tramadol, tilidine, and mixtures thereof.

2. The solid pharmaceutical composition according to claim 1, wherein said silica is anhydrous silica.

3. The solid pharmaceutical composition according to claim 1, wherein said silica is hydrated silica.

4. The solid pharmaceutical composition according to claim 1 comprising guar flour in an amount of from 150 mg to 250 mg.

5. The solid pharmaceutical composition according to claim 1 comprising guar flour in an amount of about 200 mg.

6. The solid pharmaceutical composition according to claim 1, wherein said guar flour has an average diameter lower than 100 µm.

7. The solid pharmaceutical composition according to claim 1, wherein said guar flour has an average diameter of from 10 µm to 80 µm.

8. The solid pharmaceutical composition according to claim 1, wherein said water soluble diluent is selected from the group consisting of a maltodextrin, powdered sucrose, crystalline sucrose, lactose, dextrose, mannitol, sorbitol, xylitol, and mixtures thereof.

9. The solid pharmaceutical composition according to claim 1, wherein said water soluble diluent has an average diameter lower than 500 µm.

10. The solid pharmaceutical composition according to claim 1, wherein said water soluble diluent has an average diameter of from 20 µm to 350 µm.

11. The solid pharmaceutical composition according to claim 1 comprising a secondary active ingredient, without potential for abuse, that is an analgesic.

12. The solid pharmaceutical composition according to claim 1, wherein said composition, when dissolved in about 10 mL of water, shows an osmolarity equal to or higher than 600 mOsM.

13. The solid pharmaceutical composition according to claim 1, wherein said active ingredient with potential for abuse is oxycodone.

14. The solid pharmaceutical composition according to claim 1, wherein said silica and said guar flour are present in a mass ratio of 0.5:1 or less.

15. The solid pharmaceutical composition according to claim 1, wherein said silica and said guar flour are present in a mass ratio of 0.25:1 to 0.5:1.

16. The solid pharmaceutical composition according to claim 1, wherein said guar flour has an average diameter of from 30 µm to 80 µm.

17. The solid pharmaceutical composition according to claim 1, wherein said water soluble diluent is present in an amount of 1500 mg to 3500 mg.

18. The solid pharmaceutical composition according to claim 10, wherein said water soluble diluent has an average diameter of from 40 µm to 300 µm.

\* \* \* \* \*